US009873842B2

(12) United States Patent
Cheiky et al.

(10) Patent No.: US 9,873,842 B2
(45) Date of Patent: Jan. 23, 2018

(54) SYSTEM AND PROCESS FOR BIOMASS CONVERSION TO RENEWABLE FUELS WITH BYPRODUCTS RECYCLED TO GASIFIER

(71) Applicant: Cool Planet Energy Systems, Inc., Greenwood Village, CO (US)

(72) Inventors: Michael Cheiky, Thousand Oaks, CA (US); Rajashekharam Malyala, Camarillo, CA (US); Vern S. Traxler, Simi Valley, CA (US)

(73) Assignee: COOL PLANET ENERGY SYSTEMS, INC., Greenwood Village, CO (US)

( * ) Notice: Subject to any disclaimer, the term of this patent is extended or adjusted under 35 U.S.C. 154(b) by 608 days.

(21) Appl. No.: 13/681,289

(22) Filed: Nov. 19, 2012

(65) Prior Publication Data

US 2013/0131196 A1 May 23, 2013

Related U.S. Application Data

(60) Provisional application No. 61/562,935, filed on Nov. 22, 2011.

(51) Int. Cl.
*C10G 2/00* (2006.01)
*C10L 1/00* (2006.01)
(Continued)

(52) U.S. Cl.
CPC ............. *C10L 1/00* (2013.01); *B01J 19/0046* (2013.01); *C07C 41/01* (2013.01); *C10G 1/002* (2013.01);
(Continued)

(58) Field of Classification Search
CPC . C10G 1/002; C10G 1/02; C10G 2/32; C10G 2300/1011; C07C 41/01;
(Continued)

(56) References Cited

U.S. PATENT DOCUMENTS 4,138,325 A    2/1979  Beuther et al.
2010/0125107 A1    5/2010  Lee et al.
(Continued)

FOREIGN PATENT DOCUMENTS

WO    WO-2011060539 A1    5/2011

OTHER PUBLICATIONS

Patent Cooperation Treaty, PCT International Search Report for PCT/US2012/065931, dated Jan. 29, 2013, p. 1-2.
(Continued)

*Primary Examiner* — Jafar Parsa
(74) *Attorney, Agent, or Firm* — Wilmer Cutler Pickering Hale and Dorr LLP

(57) ABSTRACT

This invention relates generally to a method and system for improving the conversion of carbon-containing feed stocks to renewable fuels, and more particularly to a thermal chemical conversion of biomass to renewable fuels and other useful chemical compounds, including gasoline and diesel, via a unique combination of unique processes. More particularly, this combination of processes includes (a) a selective pyrolysis of biomass, which produces volatile hydrocarbons and a biochar; (b) the volatile hydrocarbons are upgraded in a novel catalytic process to renewable fuels, (c) the biochar is gasified at low pressure with recycled residual gases from the catalytic process to produce synthesis gas, (d) the synthesis gas is converted to dimethyl ether in a novel catalytic process, and (e) the dimethyl ether is recycled to the selective pyrolysis process.

8 Claims, 12 Drawing Sheets

(51) Int. Cl.
*C10G 1/02* (2006.01)
*C10G 1/00* (2006.01)
*C10L 1/04* (2006.01)
*C10L 1/02* (2006.01)
*C07C 41/01* (2006.01)
*C10J 3/62* (2006.01)
*B01J 19/00* (2006.01)
*B01J 29/40* (2006.01)
*C10B 53/02* (2006.01)

(52) U.S. Cl.
CPC ............... *C10G 1/02* (2013.01); *C10G 2/32* (2013.01); *C10J 3/62* (2013.01); *C10L 1/02* (2013.01); *C10L 1/04* (2013.01); *B01J 29/405* (2013.01); *C10B 53/02* (2013.01); *C10G 2300/1011* (2013.01); *C10J 2300/0916* (2013.01); *C10J 2300/0969* (2013.01); *C10J 2300/0976* (2013.01); *C10J 2300/1656* (2013.01); *C10J 2300/1659* (2013.01); *C10J 2300/1665* (2013.01); *C10J 2300/1823* (2013.01); *Y02E 50/14* (2013.01); *Y02E 50/18* (2013.01); *Y02E 50/32* (2013.01); *Y02P 20/145* (2015.11); *Y02P 20/52* (2015.11); *Y02P 30/20* (2015.11)

(58) Field of Classification Search
CPC ............ C07C 43/043; C10J 2300/0916; C10J 2300/1656; C10J 2300/1659; C10J 2300/1665; C10B 53/02; Y02E 50/32; Y02E 50/14
USPC ........................................................ 518/700
See application file for complete search history.

(56) References Cited

U.S. PATENT DOCUMENTS

| | | |
|---|---|---|
| 2010/0180805 A1 | 7/2010 | Cheiky |
| 2010/0223839 A1 | 9/2010 | Garcia-Perez et al. |
| 2010/0228062 A1 | 9/2010 | Babicki et al. |
| 2010/0237291 A1 | 9/2010 | Simmons et al. |
| 2011/0114144 A1* | 5/2011 | Green .................... C05D 9/00 136/201 |

OTHER PUBLICATIONS

Extended European Search Report issued by the European Patent Office for European Patent Application No. 12850942.9 dated Jun. 24, 2015 (8 pages).

* cited by examiner

Experiment 1 – Front End

| | | | |
|---|---|---|---|
| ID: | VRS102 | Carrier: | $CO_2$ at 8 psi |
| Date: | 10/27/2011 | Product SG: | 0.84 |
| Feeds: | 200 gr fine grade corn cobs | Total product: | 86.5 gr |
| | 180 gr corn cobs (est. dry basis) | Char: | 63 gr |
| | 227 gr DME (total feed: 407 gr) | Liquid m-m conversion: | 86.5/407 = 21.3% |

Experiment 2 – Bubbler

ID: 90 (set of 3 batches)
Date: 9/21/2011
Batch time: ~2 hours

Experiment description

Fractionator gases were bubbled through chilled liquid fuel for a period of ~2 hours. At the end of the period, the weight gain is summarized below:

|  | Batch 1 | Batch 2 | Batch 3 |
|---|---|---|---|
| Starting liquid fuel: | 255.5 gr | 251.5 gr | 254.5 gr |
| Liquid fuel post lights condensation: | 273.5 gr | 277.0 gr | 279.5 g |
| % mass gain: | 7.0% | 10.1% | 9.8% |

Fig. 5

Experiment 3 – Back-End Process Run from Corn Cobs

Approximate overall stoichiometry $1.1\ H_2O + C \rightarrow 0.9\ CO + 0.1\ CO_2 + 1.1\ H_2 \rightarrow 0.3\ CH_3OCH_3 + 0.4\ CO_2 + 0.2\ H_2$

Experiment 3 (cont.)
Biochar Gasifier Output (Mass Spec snapshot) – DME catalyst feed

- 0.16 cc/min process water + biochar @ 900C → 400 sccm syngas
- Mass spec shows hydrogen whereas previous GC is not sensitive to hydrogen

Experiment 4. Methane + CO$_2$ to Syngas
BMF Corn Cob Char - Best Tested

SYSTEM AND PROCESS FOR BIOMASS CONVERSION TO RENEWABLE FUELS WITH BYPRODUCTS RECYCLED TO GASIFIER

REFERENCE TO RELATED APPLICATIONS

This application claims priority to U.S. Provisional Patent Application No. 61/562,935, filed on Nov. 22, 2012, the content of which is incorporated herein by reference in its entirety.

TECHNICAL FIELD

The present invention relates generally to renewable fuels, and more particularly to a method and system for thermo-chemical biomass-to-liquids conversion using in situ generated carbon and recycled water, carbon dioxide, and light hydrocarbons.

DESCRIPTION OF THE RELATED ART

Intense interest presently exists for converting biomass to transportation fuels. Two principal ways for achieving this conversion are enzymatic methods and thermo-chemical methods. The efficiency of enzymatic methods tend to be very high, but are limited by the kinetics of critical enzyme reactions. Thermo-chemical methods, on the other hand, typically possess very fast kinetics but suffer from low conversion efficiencies. It is desirable to find a high conversion efficiency thermo-chemical method thereby exploiting the advantage of fast kinetics.

There is currently a renaissance in gas-to-liquid technology (GTL) as a result of predicted and increasing needs to expand fossil fuel production and to utilize abundant lower-cost natural gas due to the increased production of economical supplies of natural gas from shale gas, particularly in North America. Some GTL technologies have been around for decades and are commercially practiced on a large scale. These technologies are all synthesis gas based and start with natural gas as an input. Major projects include the Sasol Oryx project in Qatar, the Shell Pearl project, also in Qatar, Methanex methanol projects in Trinidad and Egypt and the Sasol Chevron Escravos GTL project in Nigeria (currently under construction). Sasol is conducting a feasibility study for building a GTL plant in the United States in Louisiana utilizing natural gas as a feedstock. Alternative feedstocks to natural gas are being sought that would render the GTL processes more cost competitive.

In particular, considerable efforts are being expended to utilize biomass as the main feedstock instead of coal or natural gas. These approaches fall under the rubric of biomass-to-liquid (BTL) conversion processes. BTL research continues worldwide, but commercial realization has not been attained. Water and carbon dioxide are ubiquitous reaction products of BTL processes and often are vented into the atmosphere. The release of these compounds represents an inefficiency in the biomass conversion system. A way of recycling these back into fuel production would increase the effective conversion of the biomass.

BRIEF SUMMARY OF EMBODIMENTS OF THE INVENTION

In contrast with other BTL systems, embodiments of the present invention entail the efficient conversion of waste water and carbon dioxide streams to make more high-value fuels and chemicals. Typically the recycling of water and carbon dioxide involves breaking strong bonds in order to generate the hydrogen. If methane and light hydrocarbons are instead used as a source of hydrogen, then the energy requirements become much less, making the process more practical. This concept is illustrated in Table 1 below, which shows standard heats of formation and dissociation energy per hydrogen molecule produced for methane and alkanes including ethane through butane. Table 1 shows the energy required to dissociate hydrogen from water is 242 kJ/mol, while the dissociation energy per hydrogen molecule varies from 25 to 37 kJ/mol depending on the alkane used. A process that is able to extract hydrogen from methane and light hydrocarbons instead of water at low pressures has an advantage over a system using steam gasification at higher pressures.

TABLE 1

| Component | Chemical Formula | Mol. Wt. | Heat of Formation kJ/mol | Dissociation Energy per $H_2$ (kJ/mol)/$H_2$ |
|---|---|---|---|---|
| Methane | $CH_4$ | 16 | −74.8 | −37.40 |
| Ethane | $C_2H_6$ | 30 | −84.68 | −28.23 |
| Propane | $C_3H_8$ | 44 | −103.85 | −25.96 |
| Butane | $C_4H_{10}$ | 58 | −126.15 | −25.23 |
| Water | $H_2O$ | 18 | −241.82 | −241.82 |

One embodiment of the invention is directed toward a method for achieving high biomass thermo-chemical conversion to liquid fuels, comprising: decomposing biomass to create volatile hydrocarbons and a carbonaceous solid; catalytic upgrading of the volatile hydrocarbons to liquid fuels; gasifying the output carbonaceous solid to produce synthesis gas; catalytic upgrading of synthesis gas to fuel or fuel precursors; and recycling of byproduct streams from the catalytic upgrading to liquid fuels process.

Another embodiment of the invention is directed toward a system for achieving high biomass thermo-chemical conversion to liquid fuels, comprising: means for decomposing biomass to create volatile hydrocarbons and a carbonaceous solid; means for catalytic upgrading of the volatile hydrocarbons to liquid fuels; means for gasifying the output carbonaceous solid to produce synthesis gas; means for catalytic upgrading of synthesis gas to fuel or fuel precursors; and means for recycling of byproduct streams from the catalytic upgrading to liquid fuels process.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

FIG. 5 is a chart showing data for Experiment 2 demonstrating the % mass gain attained with bubbling biomass fractionator gases through chilled liquid fuel collected in experiment 1.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

In its most general form, an embodiment of the present invention is a system and method including basic components interacting to achieve high biomass thermo-chemical conversion to liquid fuels. The basic steps in the method involve: (a) biomass decomposition to volatile hydrocarbons and a carbonaceous solid, (b) catalytic upgrading of the volatile hydrocarbons to liquid fuels, (c) gasification of the output carbonaceous solid to produce synthesis gas, (d) catalytic upgrading of synthesis gas to fuel or fuel precursors, and (e) recycling of byproduct streams from the catalytic upgrading to fuels process to the thermo-chemical process step. The full nature of the invention will become evident to one of ordinary skill in the art from a full description of the drawings.

Figure 1:
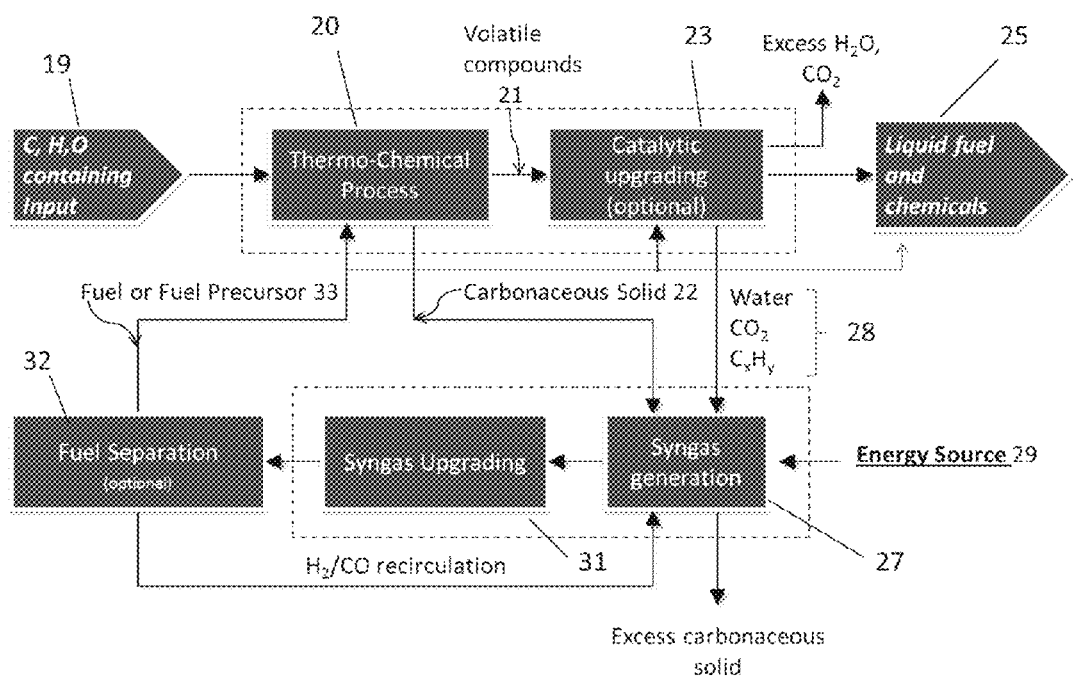
FIG. 1 is a schematic illustrating the basic components of the present invention.

FIG. 1 is a schematic illustrating the basic components of the present invention. Specifically, a substance 19 containing primarily carbon, hydrogen and oxygen (referred to herein as a "carbon-containing input") is subjected to a thermo-chemical process 20 that converts the substance to volatile compounds 21 and a carbonaceous solid 22. The substance 19 mass may contain a moderate amount of water or may be bone dry. It can include, but is not limited to, biomass, biomass-containing material, hydrocarbon-containing material, and oxygenates such as alcohols, aldehydes, ketones and ethers. Process 20 refers to any sequence of steps that convert the C,H,O-containing input 19 into volatile compounds 21 and carbonaceous solid 22. A primary requirement for process 20 involves production of a carbonaceous solid product that can be sent to a gasification process 27, and a volatile component that can be used directly or catalytically upgraded via process 23.

Process 20 can include, but is not limited to, flash pyrolysis, torrefaction, solar thermo-chemical processes, or charring. It may also include a biofractionation process which thermo-chemically converts the input at increasing temperatures under pressure. Fuels and chemicals 25 can include, but are not limited to, gasoline, gasoline-components, jet fuel, diesel, naphtha, oxygenate fuels such as methanol, higher mixed alcohols and dimethyl ether, as well as hydrogen, methane, light gas oil, ammonia, waxes and vacuum gas oil.

With continuing reference to FIG. 1, the carbonaceous solid 22 is fed to a synthesis gas generation process 27 along with the light gases output 28 from the catalytic upgrading to fuels process. Output 28 is comprised primarily of water, carbon dioxide and light hydrocarbons, typically of formula $C_xH_y$, where x=1 to 5 and y=2 to 12. An external or internal energy source may be used to power the synthesis gas generation process. Internal energy, for example, may be generated by in situ partial combustion, with air or oxygen, of the incoming light hydrocarbons. In the gasifier with external energy sources, the following reactions can occur:

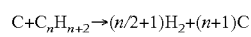

$$C + C_nH_{n+2} \rightarrow (n/2+1)H_2 + (n+1)C$$

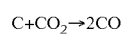

$$C + CO_2 \rightarrow 2CO$$

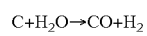

$$C + H_2O \rightarrow CO + H_2$$

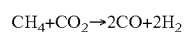

$$CH_4 + CO_2 \rightarrow 2CO + 2H_2$$

All the above reactions are endothermic. In addition, all these reactions can act simultaneously without side reactions at low pressures. As used herein, the term 'low pressures' means pressures below those typically used in conventional steam gasifiers, such as pressures below 15 bars. It may apply preferentially to pressures below 10 bars, and most preferentially below 5 bars. The synthesis gas ratio $H_2/CO$ can vary preferably from 0.1 to 5, more preferably from 0.1 to 2.5 and most preferably from produced 0.5 to 1.5. Gasification may be accomplished in apparatus known to those skilled in the art, including fixed bed gasifiers such as updraft, downdraft, downdraft multi-stage, crossdraft gasifiers, and fluid bed gasifiers such as bubbling fluidized bed and circulating fluidized bed gasifiers. Entrained flow gasifiers operating in slagging or non slagging mode are also known.

Synthesis gas produced from the gasification step is directed to a synthesis gas upgrading process 31, which converts the incoming synthesis gas into hydrocarbons and/or oxygenates. This may be accomplished via a number of different catalytic processes, including methanol and/or DME synthesis processes, Fischer-Tropsch chemistry, and synthesis gas fermentation. The product from the syngas upgrading step is directed to an optional fuel separation process 32 which separates fuel, chemicals and fuel precursors from unreacted synthesis gas and redirects the unreacted synthesis gas back to the syngas generation step or to the synthesis upgrading step. Fuel or fuel precursor 33 from the synthesis upgrading step along with any reaction side products may be redirected back to the thermo-chemical process 20 to aid in the decomposition of the carbon-containing input 19. It may also be fed to process 23 for catalytic upgrading to liquid fuel or directed to be sold as liquid fuel and chemicals 25. In this manner, a cycle is achieved which converts nominal waste water, carbon dioxide, and light hydrocarbons into high value liquid fuels and chemicals 25.

Figure 2:
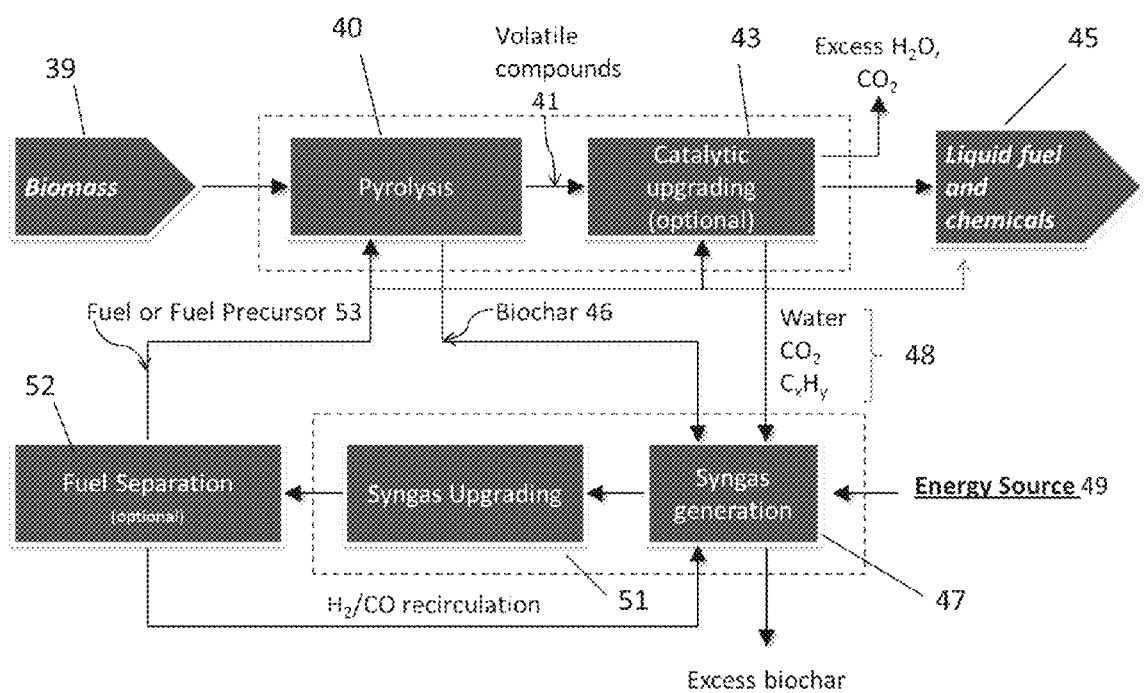
FIG. 2 is a schematic illustrating an embodiment of the present invention in which the process is pyrolysis.

FIG. 2 is a flow diagram illustrating an embodiment of the invention in which the carbon-containing input comprises biomass and the thermo-chemical process is pyrolysis. Biomass 39 is fed as input to by pyrolyzed by process 40, which concurrently outputs volatile compounds 41 and biochar 46. Process 40 may comprise any process using a limited amount of oxygen to effect a thermo-chemical process, including fast pyrolysis, intermediate pyrolysis, slow pyrolysis, pyrolysis using superheated steam or supercritical solvents. A similar cycle is described as in FIG. 1 in which water, carbon dioxide and hydrocarbons of formula $C_xH_y$, where x=1 to 5 and y=2 to 12, are fed into a syngas generation process 47 along with biochar 46 to create synthesis gas with a $H_2/CO$ that can vary preferably from 0.1 to 5, more preferably from 0.1 to 2.5 and most preferably from produced 0.5 to 1.5. Catalytic upgrading of synthesis gas may produce DME, methanol, or other chemicals, or fuels such as Fischer-Tropsch (FT) diesel or other FT products. The recycling step involves synthesis gas-derived products such as DME and methanol back to the pyrolysis step 40 and/or catalytic upgrading step 43.

As used herein, the term 'biomass' includes any material derived or readily obtained from plant or animal sources. Such material can include without limitation: (i) plant products such as bark, leaves, tree branches, tree stumps, hardwood chips, softwood chips, grape pumice, sugarcane bagasse, switchgrass; and (ii) pellet material such as grass, wood and hay pellets, crop products such as corn, wheat and kenaf. This term may also include seeds such as vegetable seeds, sunflower seeds, fruit seeds, and legume seeds. Biomass can also include: (i) waste products including animal manure such as poultry derived waste; (ii) commercial or recycled material including plastic, paper, paper pulp, cardboard, sawdust, timber residue, wood shavings and cloth; (iii) municipal waste including sewage waste; (iv) agricultural waste such as coconut shells, pecan shells, almond shells, coffee grounds; and (v) agricultural feed products such as rice straw, wheat straw, rice hulls, corn stover, corn straw, and corn cobs.

Figure 3:
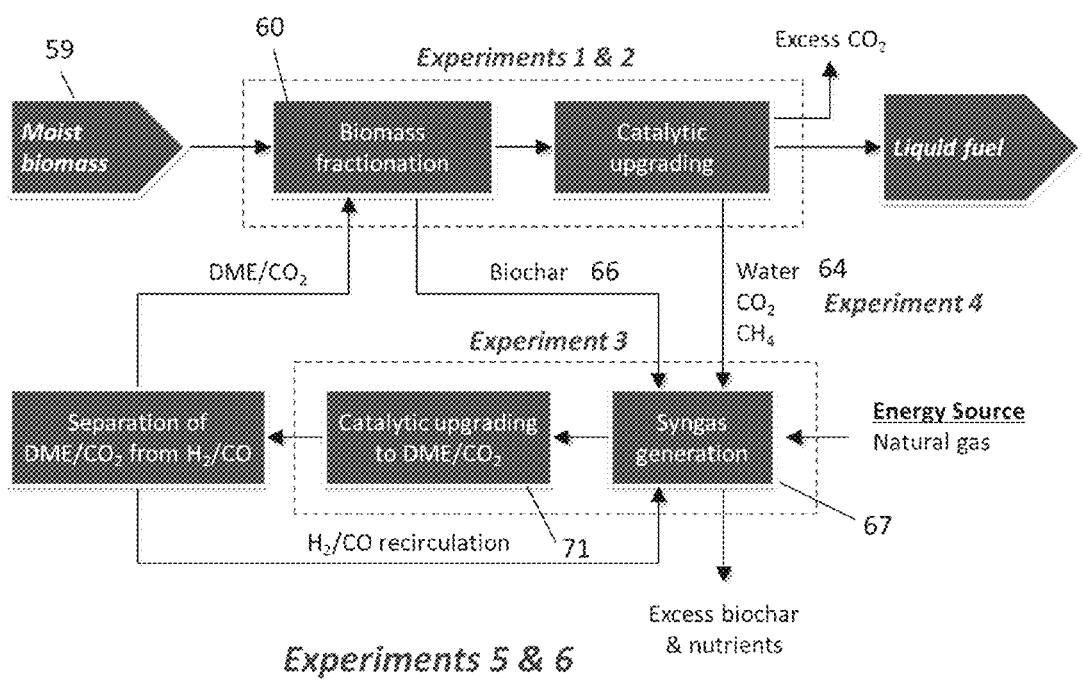
FIG. 3 is a schematic illustrating an embodiment of the present invention in which the process comprises biomass fractioning and the synthesis gas catalytic upgrading produces dimethyl ether and carbon dioxide. Relevant Experiments 1 to 6 for component performance are shown.

FIG. 3 is a flow diagram illustrating an embodiment of the present invention in which moist biomass 59 is the C,H,O-containing input and biofractionation 60 is the pyrolysis process which simultaneously produces biochar 66 and volatile components in clean and substantially uncontaminated forms. The biofractionation process subjects the biomass to decomposition using temperature ramps with the simultaneous application of pressure shocks. It is described in detail in co-owned U.S. patent application Ser. Nos. 13/103,905 and 13/019,236, the contents of which are incorporated herein by reference in their entireties. Briefly, the biomass fractionation process is a selective pyrolysis of the biomass which arises out of the interplay between the applied pressure pulses, applied temperature and resultant pressures and temperatures experienced by the biomass. Pressure shocks are applied via a compacting station with an unspecified rest time. The process starts out by utilizing the thermal conductivity of water. The biomass is first subjected to a temperature ramp sufficient to cause the biomass to release water. The released heated water vapor is then subjected to a pressure shock which compresses the steam, thus accelerating the biomass decomposition. It may be possible for the steam to attain supercritical form.

A short time after peak pressure is applied, the compacting station is pushed back by the pressure of extracted volatile compounds. When the volatile compounds are removed along with the steam, pressure within the biomass is decreased suddenly. Biomass temperature rapidly returns to base levels, and the anvil returns to its un-extended base position. After the water has been removed entirely from the biomass, the applied temperature causes hot localized areas within the biomass which initiate carbon formation. In turn, compressive impacts on the newly formed carbon increase the thermal conductivity of the carbon. The increased thermal conductivity serves to efficiently transmit heat energy needed to break down the biomass to the next stage in its decomposition. Furthermore, because carbon exhibits compressional memory, compressive impacts are sufficient to exert this effect on thermal conductivity. In this manner successive increments in temperature, accompanied by pressure shocks, lead to a selective and mild pyrolysis of the biomass along with tar-free biochar.

With continued reference to FIG. 3, the biochar 66 produced via the fractionation process 60 may be activated in situ or ex situ prior to reaction in the gasifier. An activation of the biochar creates an ultra high surface area for the reaction of methane and other light hydrocarbons. The biochar can be reacted with a stream 64 of water, carbon dioxide, methane and other light hydrocarbons in syngas generation system 67 at low pressures to produce synthesis gas close to 1/1 hydrogen to carbon monoxide ratio. This process thus allows use of low-cost natural gas in the production of high-value fuels and chemicals. The synthesis gas is catalytically upgraded to dimethyl ether, methanol and carbon dioxide in process 71 using a novel low pressure catalyst operating below 15 bar. The product dimethyl ether, methanol, and carbon dioxide is fed back into the biomass fractionation process 60 to aid in the decomposition of the biomass. In this manner, a closed recycle or feedback loop is achieved. Experiments demonstrating the performance of various components of this system will now be described.

Pyrolysis Experiments

Experiment 1

Figure 4:
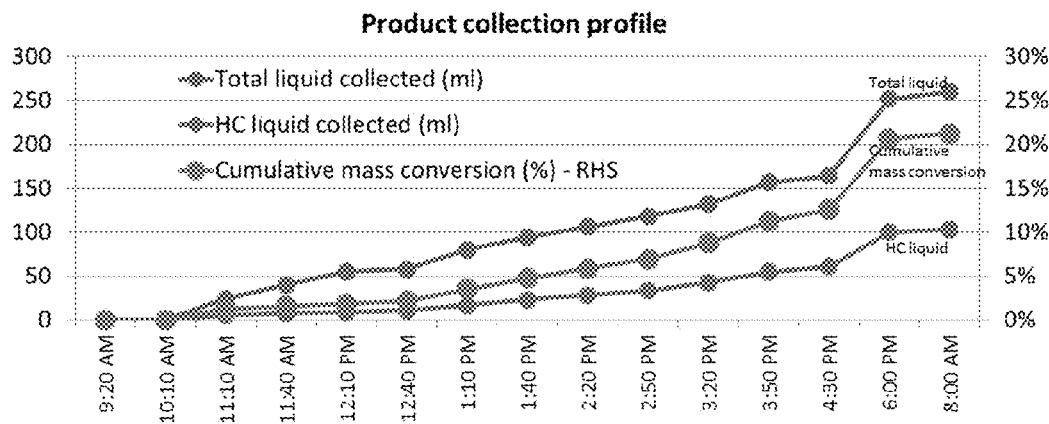
FIG. 4 is a chart showing data for Experiment 1 in which product collection profile is shown as a function of time for the front end component of the system which comprises biofractionation and catalytic upgrading to liquid fuels.

This example, as shown in FIG. 4, illustrates efficiency data from a pyrolysis system that treats biomass and a product from a catalytic upgrading process to create liquid fuel. A stainless steel tubular reactor system was loaded with 200 g of fine grade corn cobs containing 10% water. 227 g of dimethyl ether was co-fed into the biomass fractionation unit 60 using a $CO_2$ carrier gas at 8 psi. The biomass temperature was incrementally increased from 275° C. to 525° C. in increments of 50° C. over a 8 hour period. Volatile compounds 41 resulting from the biomass and co-feed decomposition in unit 40 were directed to two catalyst columns in series in unit 43. The first column was comprised of a modified ZSM-5 aromatization catalyst and operated at 370° C., while the second column comprised a Ga-modified ZSM-5 catalyst maintained at 550° C. FIG. 4 shows a fuel collection profile after the volatile compounds have been passed through the catalysts. Illustrated is the number of milliliters of fuel collected (hydrocarbon liquid) at separate time intervals as well as the total volume of liquid collected (including water). 63 g of biochar 46 are produced from unit 40. The net conversion efficiency on a pure mass basis (mass liquid hydrocarbon/mass of biomass and co-feed) was measured as 21.3% after fuel was collected after an overnight waiting period.

Experiment 2

FIG. 5 demonstrates the mass conversion efficiency gains attained when the noncondensable gases from pyrolysis gases in Experiment 1 were bubbled through chilled liquid fuel for an extended period of time. Shown in the figure are the weights of three batches of 0° C. chilled liquid fuels (obtained from condensation from a separate run) and the weights of the same batches after volatile compounds were bubbled through the chilled liquid. Gain percentages of 7.0%, 10.1%, and 9.8% were observed. In combination experiments 1 and 2 show that the mass conversion efficiency from the pyrolysis can be as high as 23.4%.

Gasification and Syngas Upgrading

Experiment 3

Figure 6:
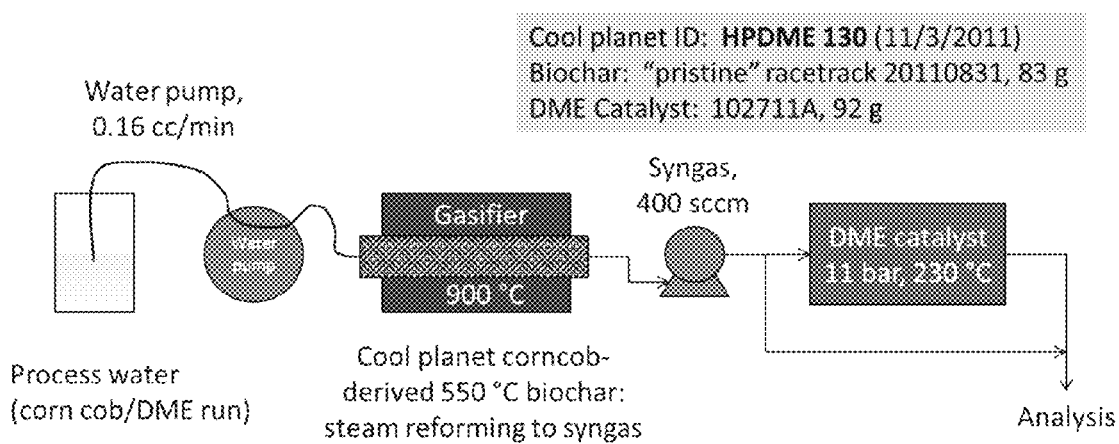
FIG. 6 is a schematic illustrating an experimental setup for Experiment 3 showing steam gasification of biofractionator biochar and subsequent synthesis gas conversion to dimethyl ether (DME).
Figure 6:
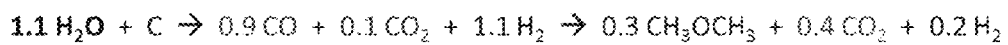
Figure 7:
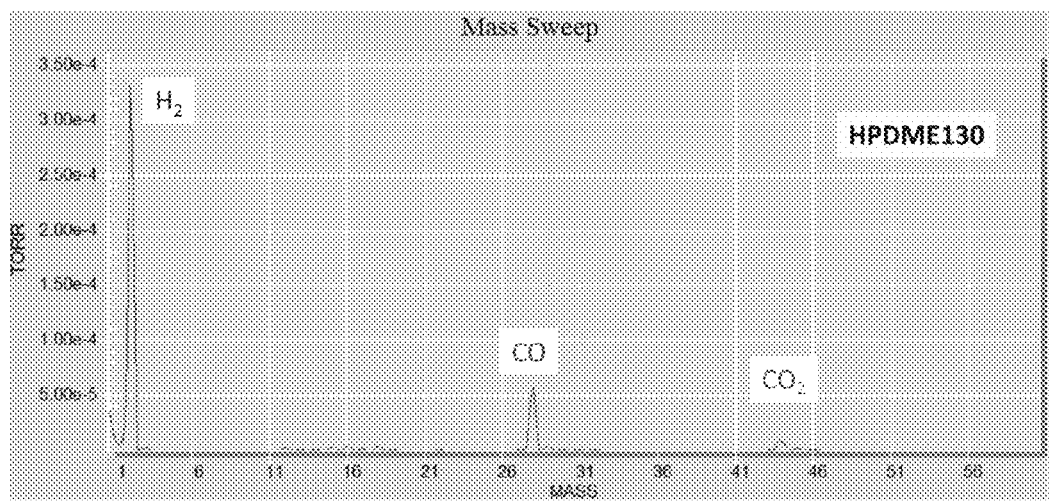
FIG. 7 is a chart showing Experiment 3 data showing mass spectrometer spectra of synthesis gas gasifier output after steam gasification of biomass fractionators-produced biochar.
Figure 8:
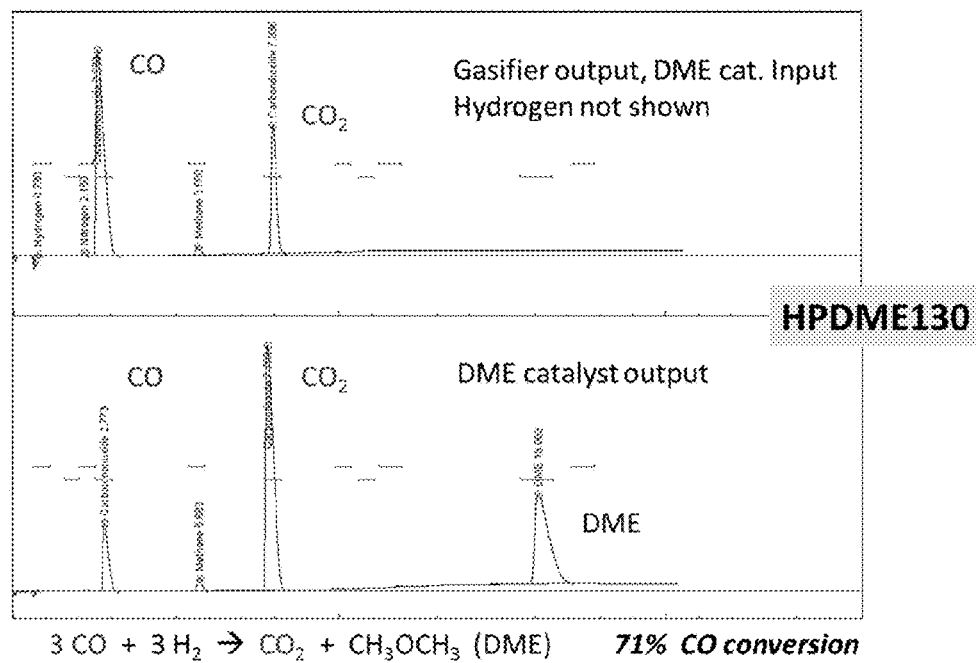
FIG. 8 is a chart showing Experiment 3 data demonstrating gas chromatographic traces of (a) synthesis gas gasifier output, and (b) catalytic upgrading to dimethyl ether output.

This experiment shows the gasification process in concert with the synthesis gas catalytic upgrading process. The experimental setup is illustrated in FIG. 6. Corn cobs were subjected to a biofractionation pyrolysis process 60 as described above. No dimethyl ether co-feed was used. 83 g of biochar 66 from the biofractionation process 60 is placed in a gasifier heated to 900° C. Process water from the biofractionation process was pumped at a rate of 0.16 ml/min to effect steam gasification and produce syngas close to ambient pressure. FIG. 7 shows mass spectrometer data of the gasifier output. Shown in the figure are partial pressures (in Torr) for hydrogen, carbon monoxide and carbon dioxide after steam gasification. From another calibration measurement, the ratio of hydrogen to carbon monoxide is close to 1. Carbon dioxide production is less than 8% of carbon monoxide production. The resulting syngas is compressed to 11 bar and directed through a proprietary dimethyl ether synthesis catalyst which exhibits a one-pass 71% CO conversion. This is demonstrated by FIG. 8, which shows gas chromatographic traces of synthesis gas gasifier output (top chart) and dimethyl ether synthesis catalyst output (bottom chart). The top chart shows the presence of carbon monoxide and carbon dioxide. Hydrogen is not shown due to low detector sensitivity. The bottom chart shows a peak corresponding to dimethyl ether and a diminished carbon monoxide peak. 71% CO conversion is calculated from the CO area changes.

Carbon Dioxide Recycling

Experiment 4

Figure 9:
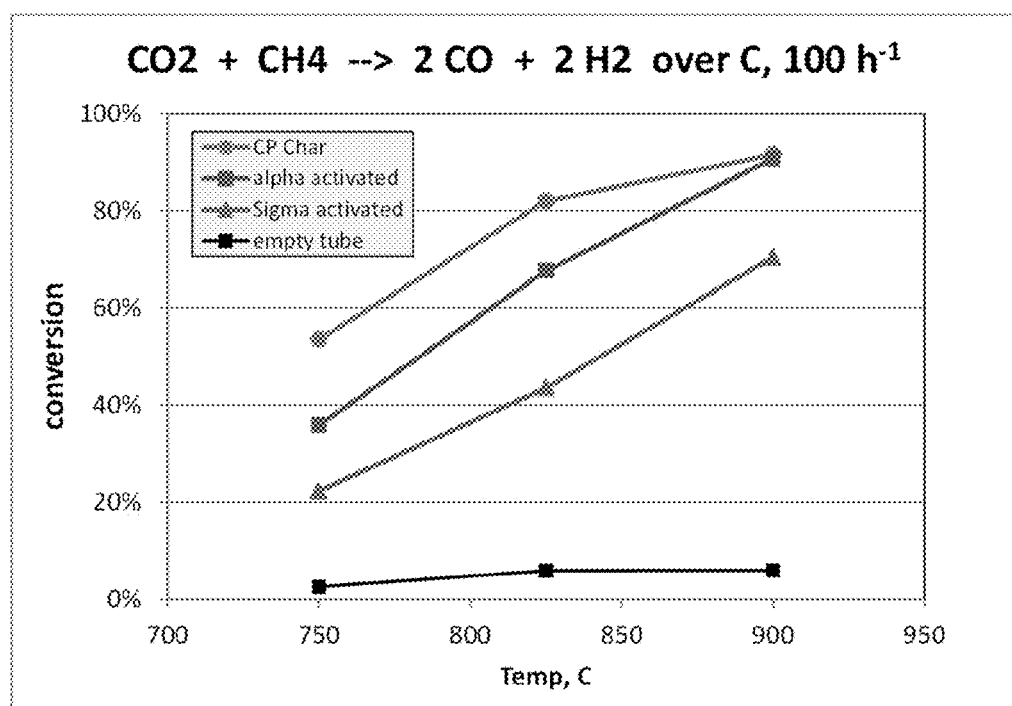
FIG. 9 is a chart showing Experiment 4 demonstrating CO2+CH4 to syngas over biochar. The data shows conversion efficiency of methane and carbon dioxide using biochar created in the present system versus two commercially available chars.

Significant amounts of carbon dioxide can be produced after the catalytic upgrading process and the dimethyl ether synthesis step. This example illustrates how this carbon dioxide can be reacted with internally or externally generated hydrocarbons, in particular methane, to generate more syngas and thus, more fuel. FIG. 9 shows the conversion rate of carbon dioxide to syngas in a gasifier at 900° C. for various biochars. The space velocity is 100 $h^{-1}$. Shown are the conversion rates for biochar created from a biofractionation process (CP char), and two commercially available chars (Alpha activated, and Sigma activated). Also shown are the results for an empty tube with no char at all. Conversion efficiencies of 90% are seen at 900° C. for both the biochar and the Alpha activated char. It is also evident that conversion efficiencies for the biochar from the biofractionation process are better at lower temperatures than the commercial activated carbon.

Integrated Pyrolysis, Gasification, and Syngas Upgrading

Experiment 5

Figure 10:
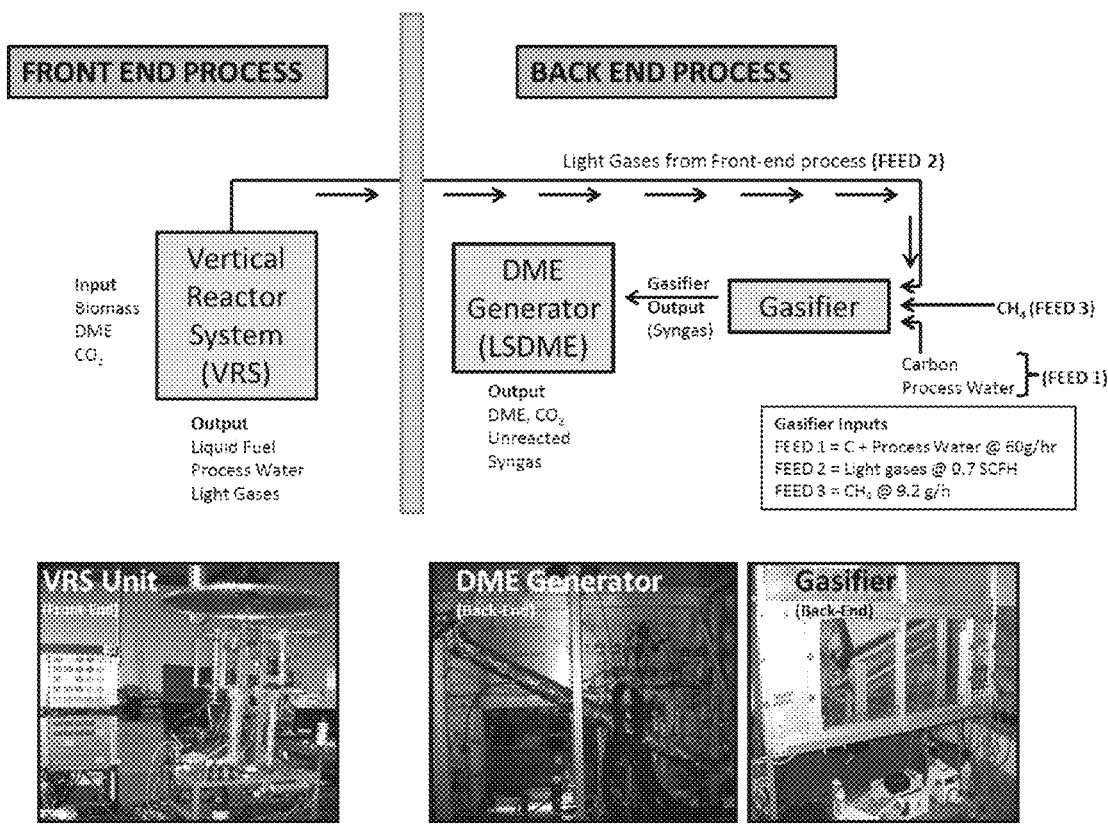
FIG. 10 is a schematic illustrating the experimental setup for Experiment 5 including basic components and various feeds.
Figure 11:
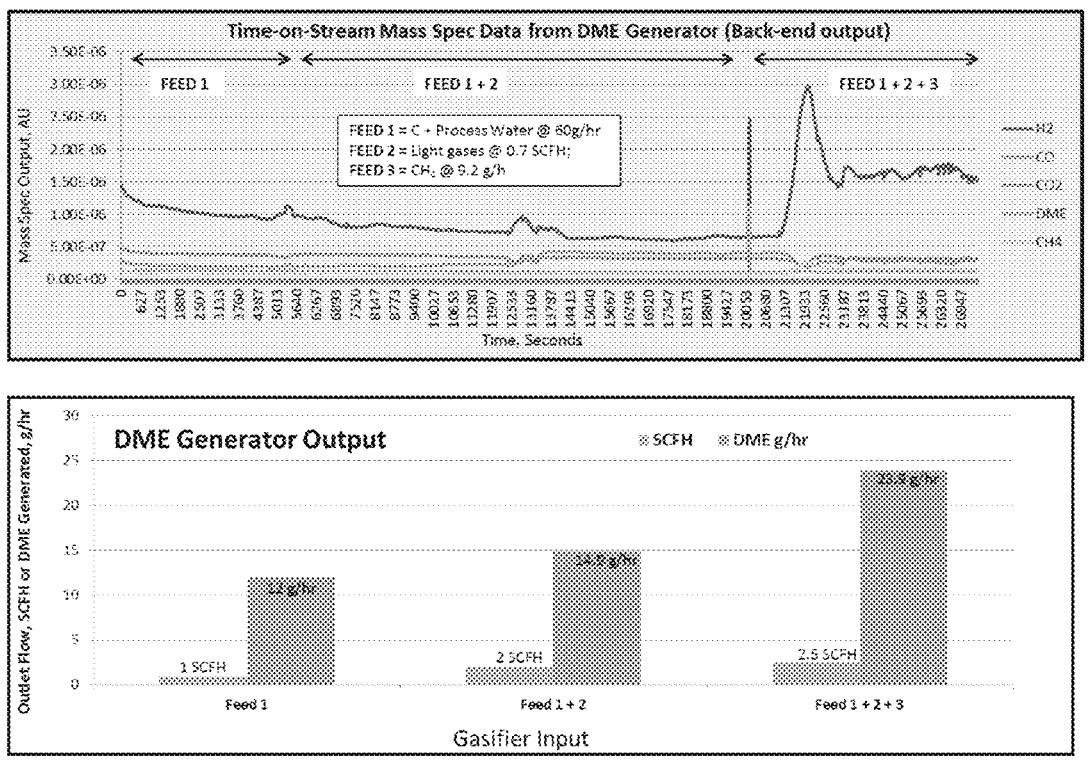
FIG. 11 is a chart showing results for Experiment 5 including (a) mass spectrometer data of various gases as a function of the feed and (b) dimethyl ether generator output as a function of the feed.
Figure 12:
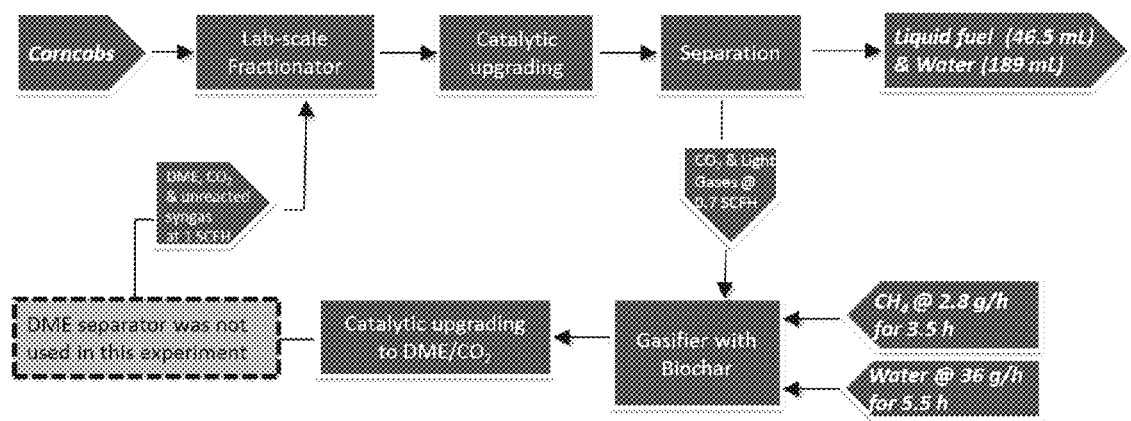
FIG. 12 is a schematic illustrating results for Experiment 6 for an integrated system utilizing recycling of by-products from the catalytic upgrading to fuels process used in the present invention in which excess corn cobs is the biomass input and excess biochar and carbon dioxide, light hydrocarbons, an external source of methane and an external source of water are fed to the gasifier.

This experiment demonstrates an integrated system using a pyrolysis process, a gasification process, and a synthesis gas catalytic upgrading process, as illustrated by FIG. 2. The experimental setup is illustrated in FIG. 10. The input comprised biomass in the form of corn cobs along with an external source of dimethyl ether was the input. Liquid fuel, process water and light gases comprising methane and other light hydrocarbons were the output from the pyrolysis process 40. The biochar 47 from the pyrolysis 40 was reacted with three different feed combinations. Process water from the pyrolysis was directed to the gasifier at a rate of 60 g/hr and this stream constitutes Feed #1. A second stream comprised of methane and light gases from the catalytic upgrading was also directed to the gasifier, and this stream flowing at 0.7 SCFH constituted Feed #2. Feed #3 comprised an external source of methane flowing at 9.2 g/hr. FIG. 11 depicts the dimethyl ether production as a function of all three feeds. Using a feed input rate of 1 SCFH, 12 g/hr of DME was generated from the steam gasification using process water. Adding the light gases and combining Feed #1 and Feed #2 increased the dimethyl ether production by 25%, to 15 g/hr. Adding methane as Feed #3 and combining all three feeds resulted in a major improvement in yield, to 24 g/hr, doubling the production over simple steam gasification.

Experiment 6

This experiment shows results for an integrated system utilizing a biofractionator as the pyrolysis unit. In this case, the biomass input comprised corn cobs, and biofractionation biochar in excess of the quantity needed for stoichiometric conversion was used in the gasifier. The gasifier received an input stream of carbon dioxide and light hydrocarbon gases at 0.7 SCFH resulting from the catalytic upgrading of volatile compounds from the fractionation process. Additionally, a separate input stream of methane of 2.8 g/hr and a separate input stream of water at 36 g/hr were also directed to the gasifier. The syngas from the gasification was catalytically upgraded to dimethyl ether and carbon dioxide. No dimethyl ether separation was effected in this experiment. Instead, all the products from the catalytic upgrading were recycled to the biomass fractionator to complete the loop. 46.5 ml of liquid fuel and 189 ml of water were collected.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. These illustrations and their accompanying description should not be construed as mandating a particular architecture or configuration.

The invention claimed is:

1. A method for achieving high biomass thermo-chemical conversion to liquid fuels, comprising:
    decomposing biomass to create one or more volatile hydrocarbons and a carbonaceous solid;
    catalytically upgrading the volatile hydrocarbons to liquid fuels;
    gasifying the output carbonaceous solid to produce synthesis gas; and
    catalytically upgrading the synthesis gas to a fuel or a fuel precursor, wherein the fuel or fuel precursor comprises hydrocarbons and/or oxygenates.

2. The method of claim 1, further comprising recycling a byproduct stream produced during the step of catalytically upgrading the volatile hydrocarbons to liquid fuels, wherein the byproduct stream is fed to the gasification step.

3. The method of claim 1, wherein decomposing biomass to create volatile hydrocarbons and a carbonaceous solid comprises flash pyrolysis, torrefaction, solar thermo-chemical processes, or charring.

4. The method of claim 3, wherein decomposing biomass to create volatile hydrocarbons and a carbonaceous solid further comprises a biofractionation process which thermo-chemically converts the biomass at increasing temperatures under pressure.

5. The method of claim 1, wherein the liquid fuels are selected from the group consisting of: gasoline, gasoline-components, jet fuel, diesel, naphtha, oxygenate fuels, higher mixed alcohols, dimethyl ether, methane, light gas oil, ammonia and vacuum gas oil.

6. The method of claim 1, wherein catalytic upgrading the synthesis gas is accomplished via one or more methanol or DME synthesis processes, Fischer-Tropsch chemistry, or synthesis gas fermentation.

7. The method of claim 1, further comprising directing the fuel or fuel precursor to a fuel separation process.

8. The method of claim 7, wherein the fuel separation process comprises separating fuel, chemicals and fuel precursors from unreacted synthesis gas and redirecting the unreacted synthesis gas back to the step of gasifying the output carbonaceous solid or to the step of catalytically upgrading the synthesis gas.

* * * * *